United States Patent [19]

Chow

[11] 4,157,958
[45] Jun. 12, 1979

[54] INVERTED VESSEL PROCESSING METHOD FOR THE PRODUCTION OF METHANE GAS

[76] Inventor: Bernard H. Chow, 6340 Morazgan St., North Highlands, Calif. 95660

[21] Appl. No.: 887,780

[22] Filed: Mar. 17, 1978

[51] Int. Cl.² .................................................. C02C 1/14
[52] U.S. Cl. .................................... 210/12; 210/14; 210/18; 210/170; 210/188; 210/218; 210/220; 48/111; 48/197 A; 55/68
[58] Field of Search ............... 23/259.1; 61/35, 101, 61/99; 48/111, 197 A, 209; 55/68; 71/10; 210/2, 13, 12, 14, 16, 19, 170, 188, 218, 220; 423/234, 432; 252/373

[56] References Cited

U.S. PATENT DOCUMENTS

| 1,383,888 | 7/1921 | Wells | 48/209 |
|---|---|---|---|
| 1,920,626 | 9/1931 | Bragg | 423/234 |
| 2,176,196 | 10/1939 | Beamer | 423/234 |
| 2,422,394 | 6/1947 | Carter | 210/13 |
| 2,640,027 | 5/1953 | McNamee | 210/13 |
| 2,907,712 | 10/1951 | Eidsness | 210/14 |
| 2,969,280 | 1/1961 | Peck | 23/259.1 |
| 3,187,897 | 6/1965 | Walker | 210/218 |
| 3,429,128 | 2/1969 | Stafford | 61/101 |
| 3,481,868 | 12/1969 | Gilwood et al. | 210/19 |
| 3,568,836 | 3/1971 | Ray | 210/242 R |
| 3,745,773 | 7/1973 | Cunningham | 210/242 R |
| 3,749,245 | 7/1973 | Kerecz | 210/12 |
| 3,793,434 | 2/1974 | Leder | 423/234 |
| 3,909,206 | 9/1975 | Katz | 55/68 |
| 3,933,628 | 1/1976 | Varani | 210/12 |
| 3,965,687 | 6/1976 | Shaw | 61/99 |

FOREIGN PATENT DOCUMENTS

| 2272726 | 12/1975 | France | 71/10 |
|---|---|---|---|
| 8011443 | 9/1958 | United Kingdom | 210/16 |

Primary Examiner—Charles N. Hart
Assistant Examiner—Ernest G. Therkorn
Attorney, Agent, or Firm—Joseph P. Nigon

[57] ABSTRACT

An apparatus for manufacture of combustible gas consisting principally of methane with minor amounts of carbon monoxide, carbon dioxide and hydrogen from organic wastes comprising an inverted vessel positioned in a body of water in a matter of such that the water acts as a "liquid door" to trap plant material and gas within the vessel.

The combustible gas manufacturing method provided by the apparatus operates at a temperature of about 21° C. to 37.8° C. Under ideal conditions it is possible to produce as much as about 11 cubic foot of gas per pound of organic waste. A moving current of water agitates the organic material and sweeps the waste products from the bottom of the vessel where they may be recovered and used as fertilizer if desired.

9 Claims, 2 Drawing Figures

INVERTED VESSEL PROCESSING METHOD FOR THE PRODUCTION OF METHANE GAS

BACKGROUND OF THE INVENTION

1. Field of the Invention

The invention relates to methods and apparatus for the manufacture of a combustible gas, principally methane. More particularly, it is concerned with the utilization of organic wastes such as grass clippings, leaves, sewage sludge, etc. as a source material for the production of a combustible gas, principally methane. The residue, swept from the bottom of the vessel by a moving current of water, may be recovered for use as fertilizer if desired.

2. Description of the Prior Art

The production of methane gas by bacterial decomposition of organic materials is well known. The accumulation of methane over swampy areas has been observed for at least 100 years. More recently the accumulation of methane in the vicinity of trash landfilled areas has been noted with some concern.

Millions of pounds of organic waste and trash are generated daily in the United States. Up to the present time the method of disposal of these materials has been in the so-called sanitary landfills. It has been recognized from time to time that the disposal of such wastes is a potential source of valuable energy and that thus energy could be recovered in the form of a combustible gas principally methane, with minor amounts of carbon monoxide, carbon dioxide and hydrogen, by the bacterial decomposition of this organic waste in a controlled manner.

There are several patents that disclose the pyrolysis of organic wastes to recover various gas and hydrocarbon fractions. U.S. Pat. No. 3,852,048 relating to a process for the production of industrial fuels from waste woody materials and U.S. Pat. No. 1,383,888 relating to a process for carbonizing wood and other carbonaceous materials are representative of the art in this area.

Although the pyrolysis systems produce a satisfactory product, they require the use of a substantial amount of heat which tends to reduce the economic value of the systems.

OBJECTS

A principal object of the invention is the provision of a new method of manufacture of methane gas from organic wastes without requiring the addition of outside heat. Another object of this invention is to provide an apparatus for the production of methane gas from organic wastes.

It is still another object of this invention to provide a continuous process for the production of methane gas that requires a minimum of investment and is capable of producing methane gas on a large scale commercial basis. It is another object of this invention to provide an apparatus for the production of methane gas from organic materials that is self-cleaning and does not require the removal of waste materials from the production unit.

Other objects of the present invention will become apparent from the detailed description given hereinafter. It should be understood, however, that the detailed description which indicates the preferred embodiment of the invention is given by way of illustration only since various modifications and changes within the scope of the invention will become apparent to those skilled in the art from this detailed description.

SUMMARY OF THE INVENTION

The objects of this invention are accomplished in part by a method and apparatus for manufacturing methane gas which basically comprises bacterially decomposing organic materials such as leaves, grass clippings, sewage sludge, etc. at a pH of therefore less than 7. An essential feature of the invention is the apparatus which consists of a vessel designed to be positioned in a body of water. The vessel has an inlet port for the addition of organic matter and an open bottom portion. A stream of water is periodically or continuously introduced into the vessel to stir the organic matter and to remove the converted organic waste from the vessel. The water, in which the vessel is positioned, also serves as a "liquid door" to allow transfer of materials freely within the apparatus and at the same time keep the gas trapped in the upper portion of the vessel. The vessel is equipped with one or more vent lines for removal of the gas. The gas is removed through these lines to a storage tank where it may be washed, if desired, with a fine spray of a solution of lime to remove carbon dioxide. The vent line is equipped with a valve that controls the level to which the compost is permitted to rise by regulating the amount of gas stored within the reaction vessel at any one time.

BRIEF DESCRIPTION OF THE DRAWINGS

A more complete understanding of the new method and apparatus of this invention may be obtained by reference to the accompanying drawings in which.

DESCRIPTION OF THE PREFERRED EMBODIMENTS

Figure 1:
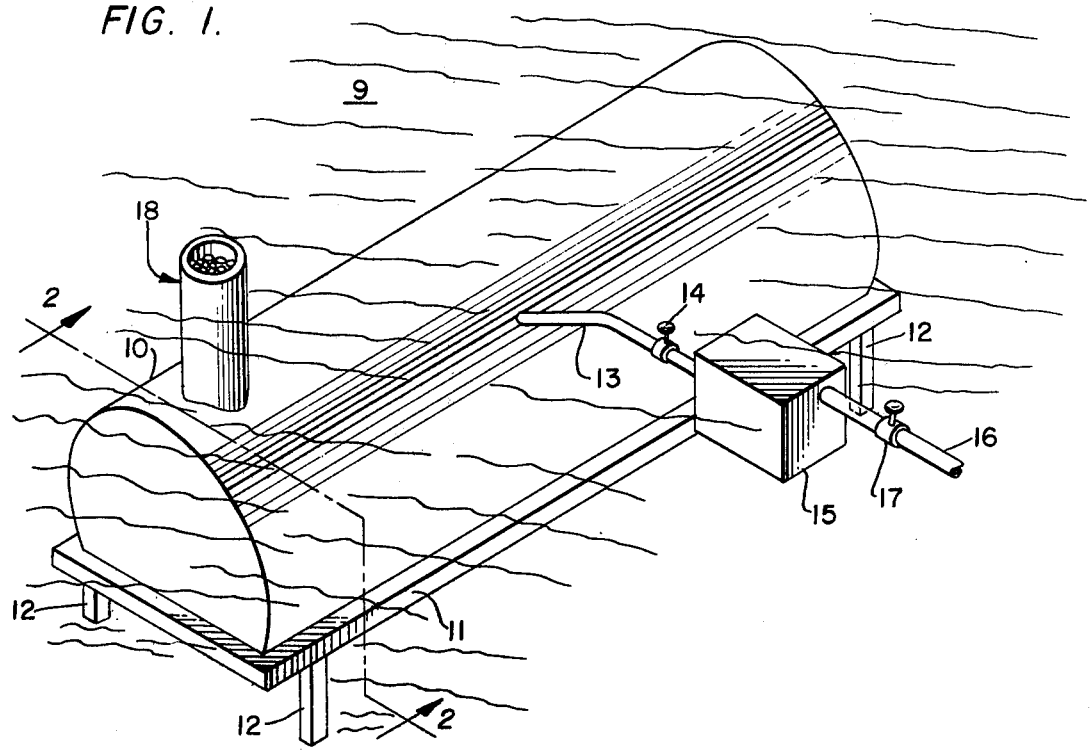
FIG. 1 is a perspective view of the apparatus taken from above.

Referring now to the drawings; FIG. 1 shows the vessel 10 positioned in a body of water shown generally as 9. The vessel is secured to the bottom of the body of water as shown at 11 & 12.

The apparatus has an inlet tube 18 for addition of organic material to the vessel and an outlet line 13, having a pressure relief valve 14, leading to a gas storage tank 15 having an outlet line 16 equipped with a conventional control unit, not shown, consisting of a pressure controlled pump. The pump is activated when the pressure in the storage tank reaches a preset level and shuts off automatically when the pressure decreases to a preset level.

Figure 2:
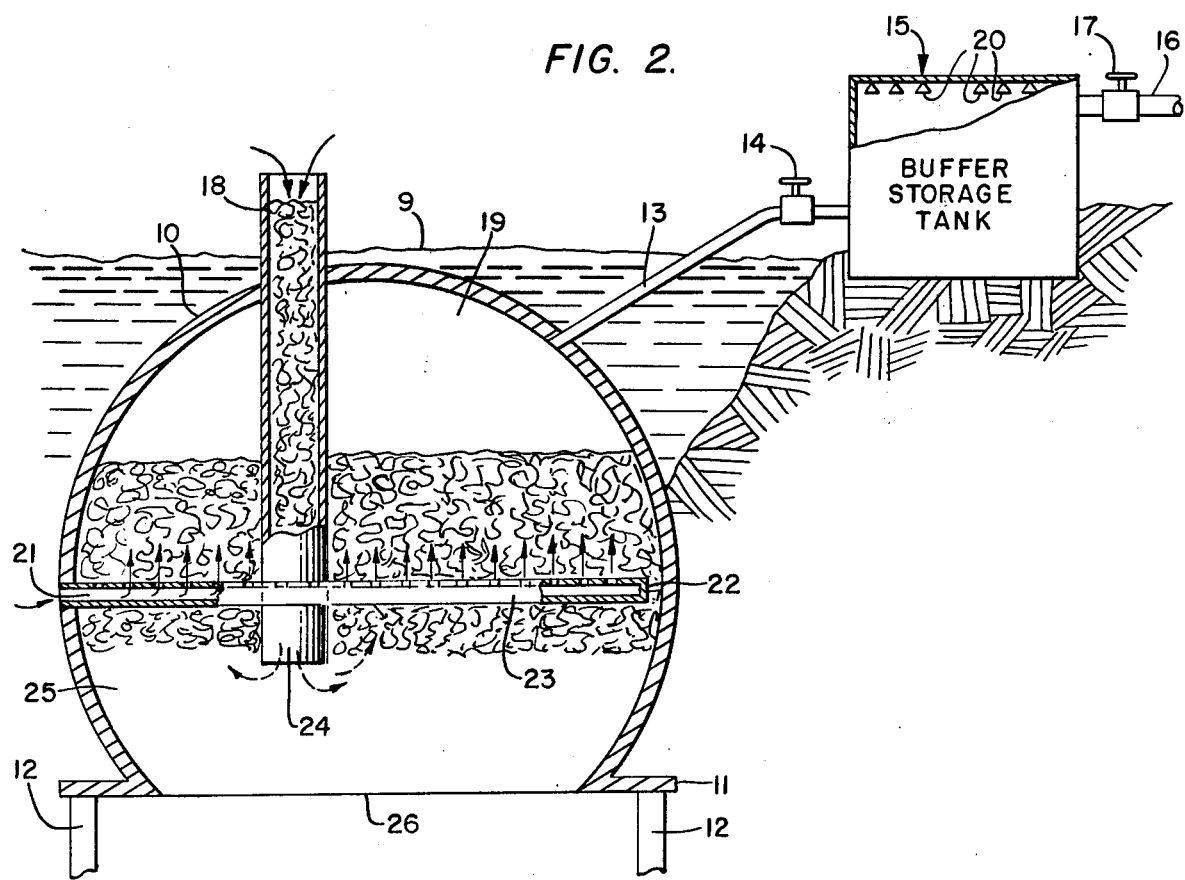
FIG. 2 is a cross-sectional view of the apparatus taken along the line 2—2 of FIG. 1.

Referring now to FIG. 2 which is a cross-section of the structure taken along the line 2—2 in FIG. 1 showing again the vessel 10 positioned in a body of water shown generally at 9. The inlet port for the organic material 18 extends through the wall of the vessel 10 to an outlet 24. The organic material fed into the vessel through the inlet port 18 drops into the body of water in the vessel and is periodically or continually agitated until the evolution of the combustible gas is completed at which time it will sink and is swept outwardly by means of the moving water in the lower portion of the vessel indicated generally at 26 that moves the digested organic material out of the vessel. The process takes about three days.

The combustible gas, consisting principally of methane with minor quantities of carbon monoxide, carbon dioxide and hydrogen, is collected in the upper portion of the vessel indicated generally at 19 and is removed through the line 13 which is equipped with a pressure relief valve 14. The line 13 is connected to a storage tank 15 which is connected to a draw-off line 16 having a valve 17. The storage tank may be equipped with jets 20 connected to a source of a washing liquid, not shown, to remove non-combustible materials such as carbon dioxide from the gas evolved by the bacterial decomposition of the organic material.

In operation of the apparatus, organic material is fed into the inlet tube 18 and drops into the body of water in the vessel designated generally at 25 through the outlet 24. The organic material is agitated by means of a jet of water that is fed at selected positions in the cross sections of the vessel through the orifice 21 by means of a pump not shown. The pump feeds water through the orifice 21 into the pipe 22 where it is moved out through the outlets in the pipe 23.

The residue is continuously removed through the open-bottom 26 by the moving water in the area 25.

The residue that collects in the bottom of the body of water outside the production unit may be recovered and used as fertilizer if desired.

My inverted vessel processing method has several advantages:

(1) The inverted vessel processing method is capable of mass production of a gas containing a large quantity of combustible gas consisting principally of methane on a large scale commercial basis.

(2) The device operates at a temperature as low as 21° C. so that no heating is required in the warm climates. Heat may be supplied when needed by heating the water supplied to the vessel.

(3) The method and apparatus allows for the continuous production of gas in the production unit without interruption for addition of new organic feed stock or removal of waste material, for the structure is self-cleaning. The movement of the water in the device removes the waste materials away from under the production unit.

(4) An essential feature of the method and apparatus is that it is safe. The internal pressure is automatically regulated. There is no danger of excessive build-up due to equipment malfunction.

(5) The structure allows a high degree of automation with only a minimum of labor.

(6) The structure is leakproof. The "liquid door" is a perfect seal.

Although the vessel is shown as a rigid vessel, it may of course be flexible if desired. The water flow may be the natural current of a stream or it may be introduced under the inverted vessel. Although the drawings show only one inlet pipe for introduction of water to stir the organic material it is obvious that these inlet pipes are spaced along the length of the vessel. It is obvious that the vessel may contain several inlet tubes rather than one as shown in the drawings.

The vessel may be made of steel, concrete, fiberglass, reinforced plastic, etc. Non-ferrous materials of construction are preferred.

What is claimed is:

1. An apparatus for converting organic waste materials to combustible gases which comprises in combination a vessel securely positioned in a body of water having at least one inlet port for addition of organic matter, an open bottom portion, at least one perforated pipe located in the lower portion of said vessel, at least one outlet port positioned near the top of said vessel for removal of the combustible gas generated, said outlet port connected to a gas storage tank, said gas storage tank being equipped with a line for removal of gas therefrom.

2. The apparatus according to claim 1 wherein said perforated structure is connected to pumps for supplying water at increased pressure into said vessel through said perforations to stir the organic matter collected in said vessel.

3. The apparatus according to claim 1 wherein a pressure relief valve is positioned between said vessel and said gas storage tank to control the volume of gas collected in said vessel.

4. The apparatus according to claim 1 wherein said gas storage tank is equipped with a spray system for introducing a washing liquid into said tank.

5. The apparatus according to claim 1 wherein said structure is secured to the bottom foundation and having an open bottom portion.

6. A method of recovering the combustible gases generated by the bacterial decomposition of organic matter which comprises:

(a) introducing said organic material into a vessel with an open bottom positioned in a body of water, (b) agitating said organic material by introducing jets of water into said vessel while maintaining the temperature in said vessel at about 70° F.-100° F. (20° C.-37.8° C.)

(c) collecting said combustible gas in the upper portion of said vessel and removing said gases to a storage tank.

7. The method according to claim 6 wherein said combustible gas is principally methane with minor amounts of carbon monoxide, carbon dioxide and hydrogen.

8. The method according to claim 6 wherein the gas collected in said storage tank is washed to remove non-combustibles.

9. The method according to claim 8 wherein the gas collected in said storage tank is washed with a solution of calcium hydroxide to remove carbon dioxide therefrom.

* * * * *